United States Patent
Singh et al.

(10) Patent No.: US 11,466,241 B2
(45) Date of Patent: Oct. 11, 2022

(54) UNIT FOR TREATMENT OF A BIOPROCESS LIQUID

(71) Applicant: CYTIVA SWEDEN AB, Uppsala (SE)

(72) Inventors: Amit Kumar Singh, Bangalore (IN); Klaus Gebauer, Uppsala (SE); Supti Datta, Bangalore (IN); Jakob Liderfelt, Uppsala (SE); Nachiket Karmarkar, Bangalore (IN); Ajit S. Vernekar, Bangalore (IN); Mats Olsson, Uppsala (SE); Rajan Thiyaga, Bangalore (IN); Amit K. Sharma, Bangalore (IN); Sasi Kumar Nutalapati, Bangalore (IN); Fredrik Lundstrom, Uppsala (SE); Jean Pierre Neff, Furdenheim (FR)

(73) Assignee: Cytiva Sweden AB, Uppsala (SE)

( * ) Notice: Subject to any disclaimer, the term of this patent is extended or adjusted under 35 U.S.C. 154(b) by 806 days.

(21) Appl. No.: 15/781,217

(22) PCT Filed: Nov. 25, 2016

(86) PCT No.: PCT/EP2016/078760
§ 371 (c)(1),
(2) Date: Jun. 4, 2018

(87) PCT Pub. No.: WO2017/097604
PCT Pub. Date: Jun. 15, 2017

(65) Prior Publication Data
US 2021/0017482 A1    Jan. 21, 2021

(30) Foreign Application Priority Data

Dec. 7, 2015 (IN) .......................... 3975/DEL/2015

(51) Int. Cl.
*C12M 1/00* (2006.01)
*B01D 15/08* (2006.01)
(Continued)

(52) U.S. Cl.
CPC ............ *C12M 23/28* (2013.01); *B01D 15/08* (2013.01); *B01D 61/18* (2013.01); *C12M 23/50* (2013.01);
(Continued)

(58) Field of Classification Search
CPC ...... C12M 23/28; C12M 29/00; C12M 41/00; C12M 23/50; C12M 29/04; B01D 15/08; B01D 61/18
(Continued)

(56) References Cited

U.S. PATENT DOCUMENTS

| 6,461,513 B1 | 10/2002 | Jen | |
|---|---|---|---|
| 2011/0101680 A1* | 5/2011 | Menor | F16L 33/2076 285/247 |
| 2013/0240065 A1* | 9/2013 | Weissenbach | B01D 63/00 137/561 R |

FOREIGN PATENT DOCUMENTS

| CN | 104897885 A | 9/2015 |
|---|---|---|
| GB | 1434786 | 5/1976 |

(Continued)

OTHER PUBLICATIONS

Chinese Office Action for CN Application No. 201680071381X dated Jul. 2, 2020 (11 pages).
(Continued)

*Primary Examiner* — Michael L Hobbs
*Assistant Examiner* — Lenora A Abel
(74) *Attorney, Agent, or Firm* — Eversheds Sutherland (US) LLP

(57) ABSTRACT

The invention discloses a first unit (1) for treatment of a bioprocess liquid comprising a first lateral face (2), a second
(Continued)

lateral face (3) and a front face (4) which meets the two said lateral faces. The front face comprises: a plurality of valves (7) adapted to receive and act upon one or more legs (8) of a disposable flow path (6); optionally one or more pumps (10) adapted to receive and act upon one or more legs of the disposable flow path; optionally one or more sensors (11) adapted to receive and to measure one or more parameters in one or more legs of the disposable flow path; wherein the plurality of valves and optional pumps and sensors are vertically offset from each other to give one or more legs of a disposable flow path received by said valves and optional pumps and sensors a slope of at least 3.0 degrees from the horizontal plane (h).

33 Claims, 7 Drawing Sheets

(51) Int. Cl.
  *B01D 61/18* (2006.01)
  *C12M 1/34* (2006.01)

(52) U.S. Cl.
  CPC .......... *C12M 29/00* (2013.01); *C12M 29/04* (2013.01); *C12M 41/00* (2013.01)

(58) Field of Classification Search
  USPC .................................................. 435/297.1
  See application file for complete search history.

(56) References Cited

FOREIGN PATENT DOCUMENTS

| WO | 03/033120 A1 | 4/2003 | |
|----|----|----|----|
| WO | 2011/161609 A1 | 12/2011 | |
| WO | WO-2011161609 A1 * | 12/2011 | ............ B01D 63/00 |
| WO | 2013/043433 A2 | 3/2013 | |
| WO | 2014/051503 A1 | 4/2014 | |

OTHER PUBLICATIONS

PCT International Search Report for PCT Application No. PCT/EP2016/078760 dated Feb. 21, 2017 (10 pages).
Indian Office Action for IN Application No. 3975/DEL/2015 dated Jun. 16, 2020 (5 pages).

* cited by examiner

UNIT FOR TREATMENT OF A BIOPROCESS LIQUID

CROSS REFERENCE TO RELATED APPLICATIONS

This application claims the priority benefit of PCT/EP2016/078760 filed on Nov. 25, 2016 which claims priority benefit of Indian Application No. 3975/DEL/2015 filed Dec. 7, 2015. The entire contents of which are hereby incorporated by reference herein.

TECHNICAL FIELD OF THE INVENTION

The present invention relates to instrumentation for treatment of bioprocess liquids, and more particularly to instrumentation for filtration of bioprocess liquids using disposable flow paths. The invention also relates to a method of installing a disposable flow path on an apparatus for filtration of bioprocess liquids.

BACKGROUND OF THE INVENTION

Crossflow filtration ("CFF" also referred to a "tangential flow filtration" (TFF)) systems are used in industry applications, such as, for example, manufacturing process separations, waste treatment plants and water purification systems where they can extend the lifetime of filtration membranes by removing and/or preventing the build-up of contaminants and promote consistency of the filtration process with time.

The most commonly used CFF/TFF membrane processes are microfiltration and ultrafiltration. Such processes may be pressure driven and depend upon the "membrane flux", defined as the flow volume over time per unit area of membrane, across the microfiltration or ultrafiltration membrane. At low pressures, the transmembrane flux is proportional to pressure. As a result, by varying the transmembrane pressure difference driving force and average pore diameter, a membrane may serve as a selective barrier by permitting certain components of a mixture to pass through while retaining others. This results in two phases, the permeate and retentate phases, each of which is enriched in one or more of the components of the mixture. The retentate stream is recirculated in the flow circuitry and is pumped across the membrane again in a continuous fashion. Such CFF/TFF systems are used to significantly reduce the volume of the sample solution as a permeate stream is withdrawn from the system. So, the sample solution becomes concentrated when the system is driven in a concentration mode.

CFF/TFF systems have the advantage that due to the direction of the flow of the fluid sample, which is essentially parallel to the membrane surface, an automatic sweeping and cleansing takes place so that higher fluxes and higher throughputs can often be attained with such systems in relation to corresponding normal flow filtration systems. Further, a large fraction of sample flows continuously over the membrane surface so that a clogging and fouling is discouraged in such systems. With respect to these and other advantages, CFF/TFF systems are often used in industrial and/or biotechnological processes.

In an automated CFF/TFF system, buffer and other system treatment solutions need to circulate through the filter and other system components for equilibration prior or subsequent to the separation process. Ideally, such circulation and equilibration of buffer and other system treatment solutions is performed by an automated method without the need for manual intervention.

Filtration systems are a critical component of the pharmaceutical and biotechnology industries for purifying bioprocessing liquids. Due to the high value of the purified liquid extensive research has been focused on improving all aspects of the filtration systems. Such filtration systems also cover a broad spectrum of utility including micro-filtration, ultrafiltration, tangential or cross-flow filtration, as well as constant volume diafiltration. Generally, in these systems, the liquid to be filtered is forced through a flow path to a porous membrane sheet or a porous hollow fiber column. Such sheets or membranes are commercially available and utilizing these different pore sizes molecules or particulates smaller than the average membrane or column pore size will pass, together with solvent for example, through the membrane or hollow fiber walls and are collected as filtrate. A retentate flow is left behind. In many filtration approaches, such as those incorporating ultrafiltration or other tangential-flow filtration devices, the retentate is repeatedly re-circulated with the objective of improving filtration efficiency and enhancing the yield of the filtrate or permeate. Each of these flows contains valuable product up to 1-5% of the total recovery potential. Examples of such systems can be found in U.S. Pat. No. 6,607,669 to Schick issued Aug. 19, 2003; U.S. Pat. No. 7,270,744 to Petersen issued Sep. 18, 2007; U.S. Pat. No. 6,461,513 and International Patent Publication WO 2014/051503 published Apr. 3, 2014, which are hereby incorporated by reference in their entireties.

Quantitative recovery of the valuable concentrated bioprocess liquid after purification and or concentration is one area of interest. Once maximal purification and/or concentration processing is complete a significant amount of residual bioprocess liquid remains in the flow path of the filtration system. Numerous strategies have been applied to facilitate recovery of this residual liquid. Unfortunately none of these methods has resulted in the efficient and quantitative recovery of all residual liquid.

Further, there is a need for removal of air from the flow path during startup of the process, which is not adequately addressed by the current art.

Accordingly there is a need for further developments to ensure complete recovery of valuable bioprocess liquids as well as complete air removal during startup. This need applies to filtration systems but also to other bioprocess systems, such as e.g. chromatography systems and bioreactors.

SUMMARY OF THE INVENTION

One aspect of the invention is to provide a unit for treatment of a bioprocess liquid which allows complete recovery of liquid and facilitates the removal of air from the system. This is achieved with a first unit as defined in claim 1.

An advantage is that the unit improves the drainage of a disposable flow path mounted on the unit prior to disposal of the flow path. It is always advantageous to to drain while the flow path is in a controlled position, i.e. mounted on the unit, compared to draining a loose flow path after dismounting it from the unit and manually directing the tubing towards a draining point. The latter procedure is not compatible with GMP manufacturing and definition of standard operating procedures necessary in a biopharmaceutical production setting.

A second aspect of the invention is to provide an apparatus for treatment of a bioprocess liquid which allows complete recovery of liquid and facilitates the removal of air from the system. This is achieved with an apparatus as defined in the claims.

A third aspect of the invention is to provide a method of installing a disposable flow path on a unit for treatment of a bioprocess liquid. This is achieved with a method as defined in the claims.

A fourth aspect of the invention is to provide a method of tangential flow filtration of a bioprocess liquid. This is achieved with a method as defined in the claims.

Further suitable embodiments of the invention are described in the dependent claims.

DRAWINGS

DEFINITIONS

Figure 1:
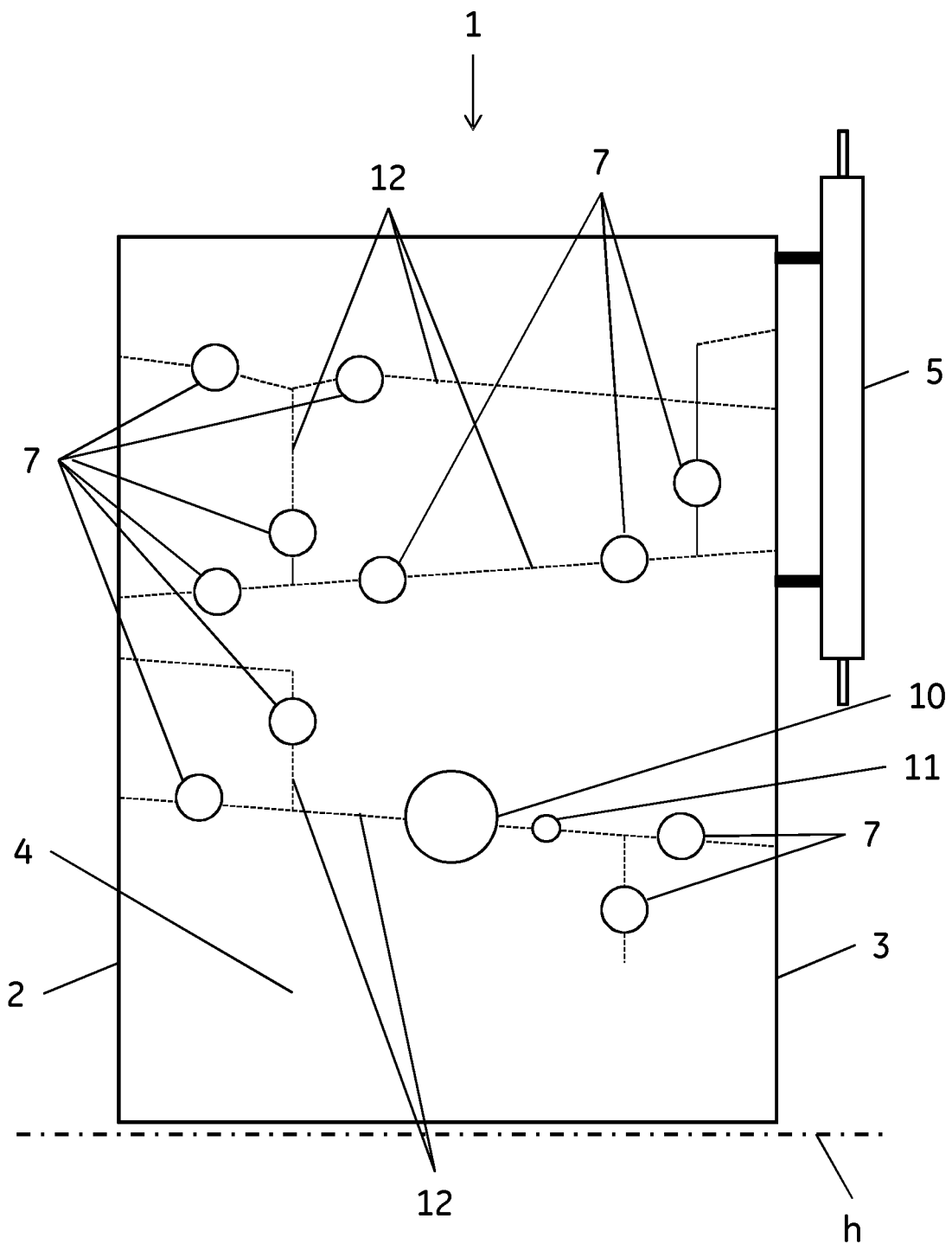
FIG. 1 shows a first unit of the invention (front view).

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

Any directional terms such as "top", "bottom", "above", "below" "up", "down", "high", "low" and "height" herein refer to the devices as they appear in the drawings. Joinder references (e.g., joined, attached, coupled, connected, and the like) are to be construed broadly and may include intermediate members between a connection of elements and relative movement between elements. As such, joinder references do not necessarily imply that two elements are connected directly and in fixed relation to each other.

Further, various elements discussed with reference to the various embodiments may be interchanged to create entirely new embodiments coming within the scope of the present invention.

DETAILED DESCRIPTION OF EMBODIMENTS

Figure 2:
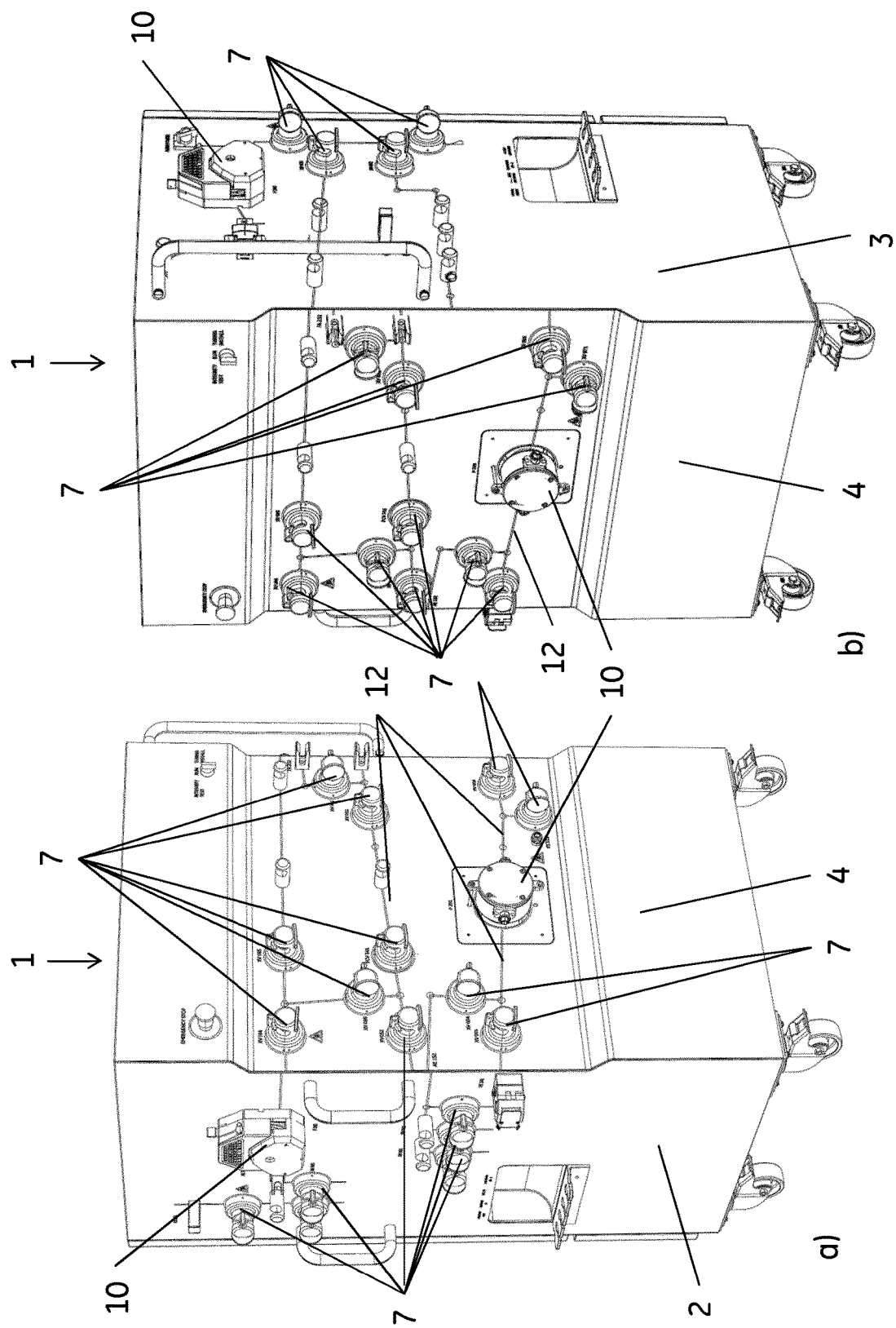
FIG. 2 shows an alternative first unit of the invention in perspective views—a) left side+front, b) right side+front.
Figure 3:
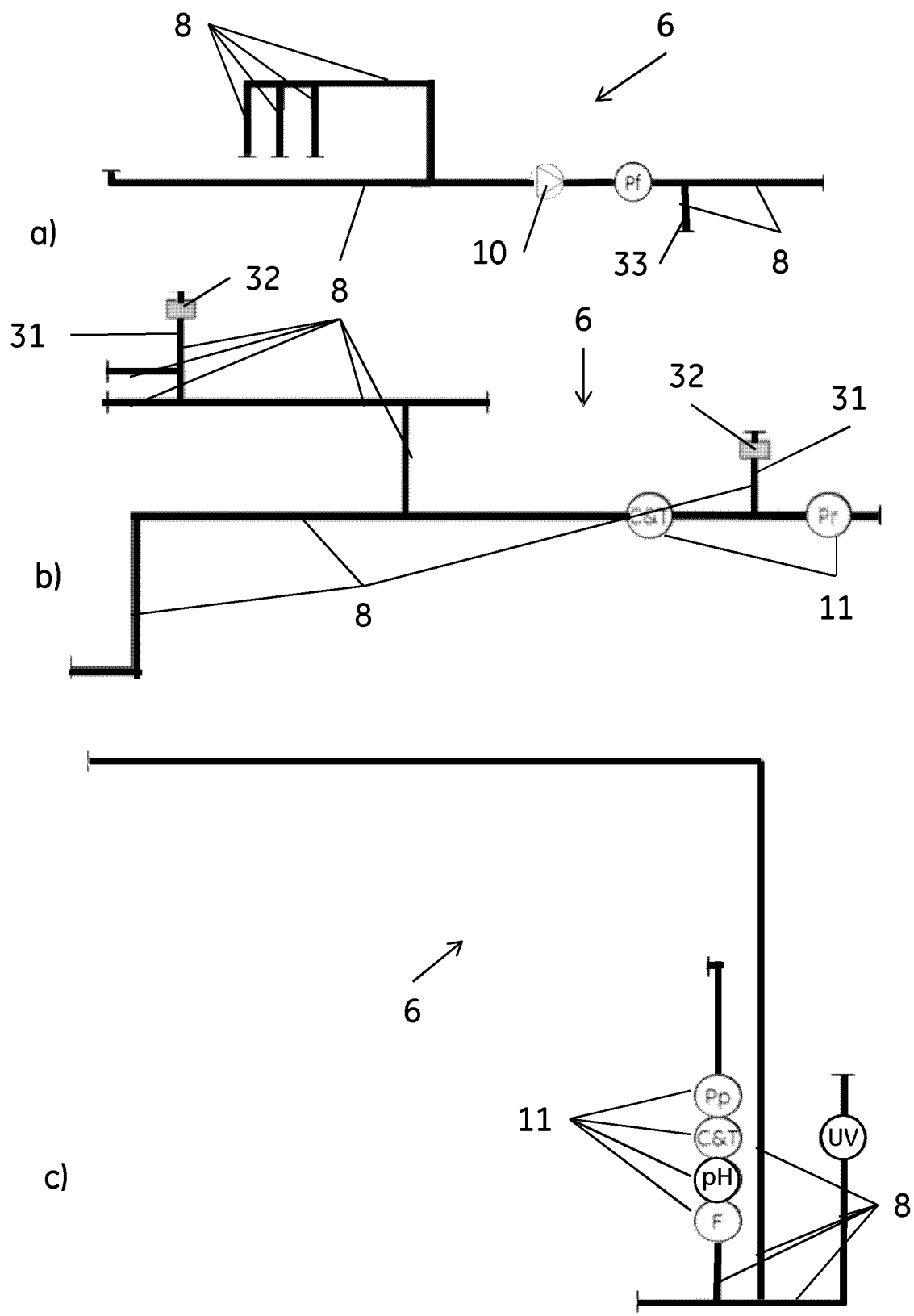
FIG. 3 shows three flow path components for use e.g. with the unit of FIG. 2 (schematic drawings with the slopes not shown). a) Feed flow path, b) Retentate flow path, c) Permeate flow path.

In one aspect, illustrated by FIGS. 1-2, the present invention discloses a first unit 1 for treatment of a bioprocess liquid, which can e.g. be a filtration unit, such as a tangential flow filtration unit or a dead end filtration unit. Alternatively, the first unit can be a chromatography unit or a bioreactor unit. The first unit comprises a first lateral face 2, a second lateral face 3 and a front face 4 which meets the two lateral faces. Suitably, the front face and optionally also the lateral faces can be vertically oriented. The first unit may comprise or be adapted to receive a filter element 5, e.g. on one of the lateral faces. This filter element may be fluidically connected to a disposable flow path 6. The first unit, in particular the front face 4, comprises:

i) A plurality of valves 7 adapted to receive and act upon one or more legs 8 of a disposable flow path, which may at least partly be attached to the front face, e.g. by being received by the valves. The valves can e.g. be pinch valves and the disposable flow path can e.g. comprise lengths of flexible tubing 8 connected by connectors 9, e.g. hose barb connectors. These connectors can e.g. be two-way connectors or three-way connectors such as Y or T connectors. In a tangential flow filtration system, the disposable flow path can e.g. comprise a feed line, a retentate loop and a permeate loop or line, where the retentate loop and the permeate loop/line are suitably fluidically connected to a filter element 5. The filter element can e.g. be a hollow fiber cartridge or one or more flat sheet membrane cassettes in a cassette holder. The flow path may also comprise additional legs for draining, air removal, and/or cleaning of the system. The flow path is disposable in that it is intended for single use and is composed of low cost plastic and/or elastomeric components suitable for pre-sterilization, e.g. by gamma irradiation. It can e.g. comprise one or more lengths of flexible tubing, such as non-braided tubing for low pressure applications and braided tubing for applications requiring higher pressures. Tubing lengths may be connected by hose barb connectors (e.g. straight connectors, Y or T connectors) and secured e.g. by cable ties or clamps such as Oetiker clamps (Oetiker+Partner AG) or BarbLock fittings (St Gobain). The inner diameter of the tubing can e.g. be 5-25 mm, such as 10-25 mm. The flow path can suitably comprise sanitary or aseptic connectors, e.g. as described in U.S. Pat. No. 6,679,529, US 2009/0015005 or US 2015/0061282 (hereby incorporated by reference in their entireties), in order to allow for aseptic connection of the pre-sterilized flow path to pre-sterilized filtration elements, tanks, bags, further flow paths etc. Examples of flow path components are shown in FIG. 3. The disposable flow path may further comprise at least one air outlet leg 31 and/or at least one draining leg 33, where the air outlet leg may be configured for letting out air from the system/flow path and may be located at a high/top position of the flow path. The air outlet leg may further be equipped with a sterilization grade filter 32 to prevent contamination of the flow path. The draining leg may be configured for draining the system/flow path and may be located at a low/bottom position of the flow path.

ii) Optionally one or more pumps 10 adapted to receive and act upon one or more legs of said disposable flow path. The pumps may e.g. be peristaltic pumps or pump drives for disposable pump heads. In the latter case, the disposable pump heads may form part of the disposable flow path and be received by the pump drives on the front face.

iii) Optionally one or more sensors 11 adapted to receive and to measure one or more parameters in one or more legs of the disposable flow path. The sensors may e.g. be pressure sensors or flow rate sensors but they can also comprise e.g. pH, conductivity or concentration sensors.

The plurality of valves and optional pumps and sensors are vertically offset from each other to give one or more legs, such as all legs, of a disposable flow path received by the valves and optional pumps and sensors a slope of at least 3, such as at least 4 degrees from the horizontal plane h. The slope can be defined as the angle α between a straight line from one end 23 of a leg 8 to an opposite end 24 of the leg and the horizontal plane h. Suitably, the slope of one or more legs can be 3.0-10.0, such as 3.0-8.0 or 4.0-6.0 degrees from the horizontal plane. The slope allows efficient draining of the system, which is essential for the recovery of valuable material after completion of a treatment, e.g. a filtration run, a chromatography run or a cell culture. This also minimizes the amount of liquid discarded with the disposable flow path after use, facilitating incineration of the flow path and reducing the amount of potentially biohazardous material to be handled as waste. Further, removal of air from the system is also facilitated by the slope. The slope is particularly important when a flow path with lengths of tubing 8 connected by hose barb couplings 9 is used, as the lower inner diameter of the hose barb couplings causes stagnating pools and can trap air bubbles. Hose barb couplings are particularly desirable for braided tubing and other types of tubing which is not amenable to connection by welding or molding. We have found that a slope larger than 3 degrees drastically improves the draining, particularly when connectors are used, but also to counteract any slack in flexible flow path legs. The volume of the flow path should generally be kept as low as possible to minimize the hold-up volume, thus allowing high concentration factors and low volumes of processed fluid. Fort this reason, the slopes can suitably be up to 10.0 degrees or up to 8.0 or 6.0 degrees, as higher slopes lead to longer legs. Short branch legs connecting the longer legs may however need to have a higher slope, e.g. about 90 degrees.

As illustrated in FIG. 2, also one or both of the lateral faces 2 and 3 may comprise a plurality of valves 7 and optional pumps 10/sensors 11 adapted to receive one or more flow path legs 8 in a sloped configuration.

Figure 7:
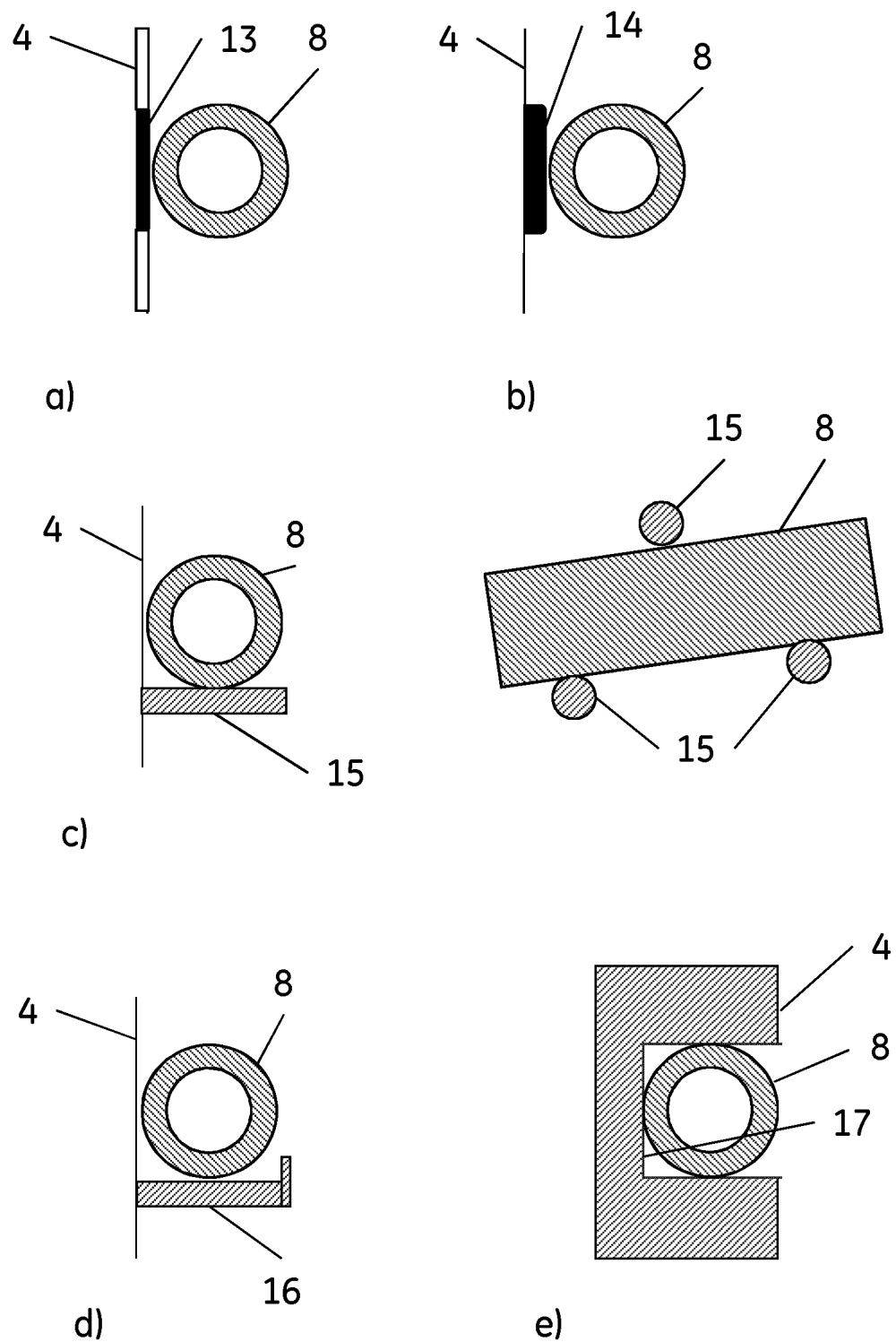
FIG. 7 shows different types of guides:
a) Coloured line (side view).
b) Relief (raised) line (side view).
c) Pegs (side and front view).
d) Ledge (side view).
e) Recess (side view).

In some embodiments, illustrated by FIGS. 1, 2 and 7, the first unit further comprises guides 12 on the front face, and optionally one or both of the lateral faces, between the valves and any optional pumps and sensors for installation of the disposable flow path. The guides can be essentially linear with slopes of at least 3.0, such as at least 4.0, or 3.0-10.0, 3.0-8.0 or 4.0-6.0 degrees from the horizontal plane. They may comprise visually and/or tactilely distinguishable lines, such as e.g. coloured lines 13 or relief lines 14 along which the legs of a disposable flow path can be arranged. The guides may also comprise means for restraining a disposable flow path with the desired slope, e.g. pegs 15, ledges 16 and/or recesses 17 adapted to receive the disposable flow path. The legs of the disposable flow path can suitably be aligned with the guides, and in case the guides comprise restraining means this can minimize any slack in flexible flow path legs. During use, single use systems for treatment of bioprocess liquids require frequent installation and removal of the flow paths. This is greatly facilitated by the presence of guides.

Figure 8:
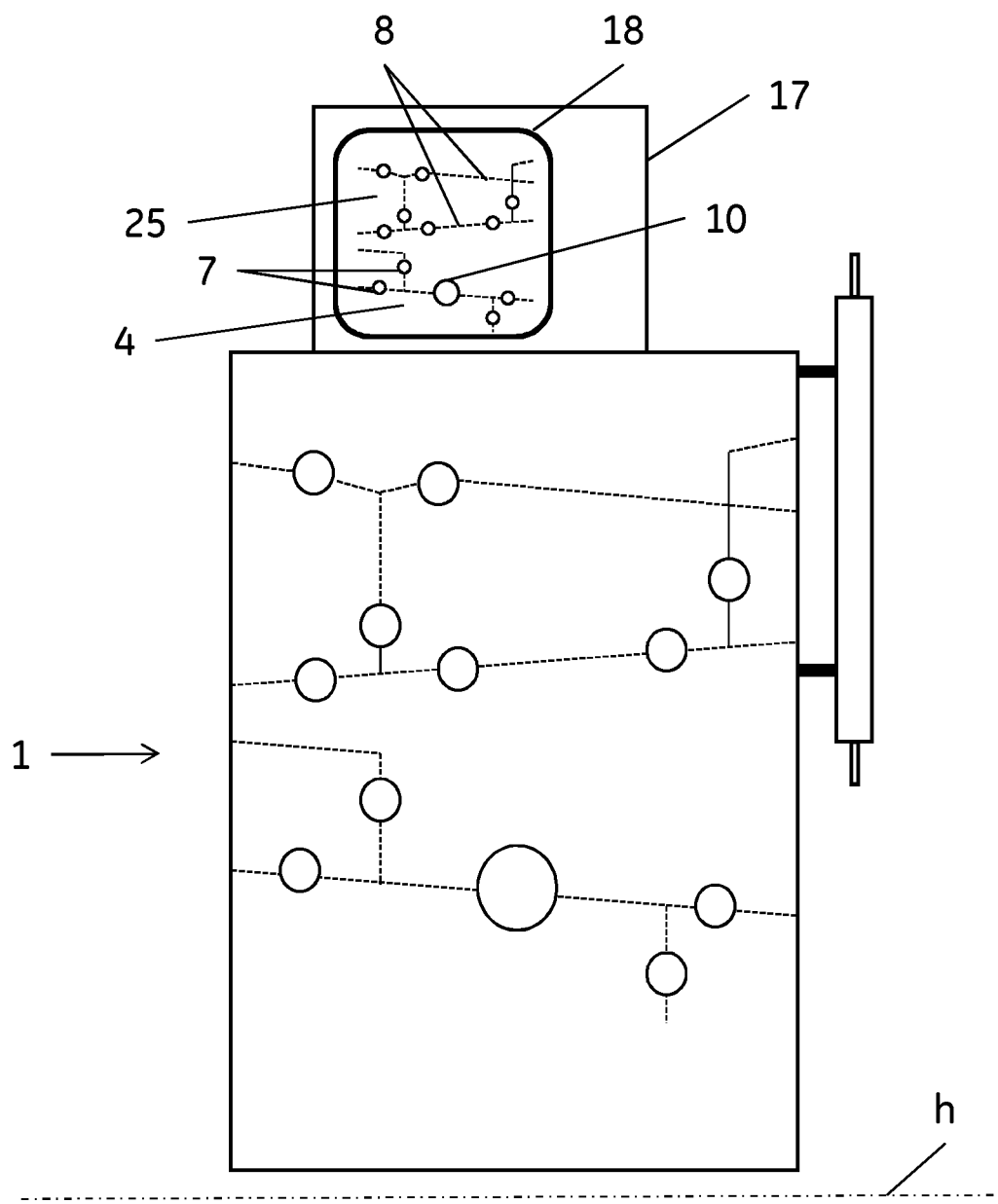
FIG. 8 shows a processor with a graphical user interface.

In certain embodiments, illustrated by FIG. 8, the first unit (or the apparatus 30 as discussed below) further comprises a processor 17 with an optical display 18. A graphical user interface 25 on the optical display shows an outline of the front face 4 with valves 7, optional pumps 10 and sensors 11 and the flow path 6, with one or more legs 8 of the flow path having a slope of at least 3.0, such as at least 4.0, or 3.0-10.0, 3.0-8.0 or 4.0-6.0 degrees from the horizontal plane h. The graphical user interface with the slopes visualized is helpful for the user to understand the orientation of the flow path legs. Further it facilitates the programming of methods for draining/recovery and/or air removal with appropriate flow directions. This is particularly important for draining/recovery methods, where the draining flow directions in the flow path may be the reverse of the pump flow directions during the main process operation.

Figure 4:
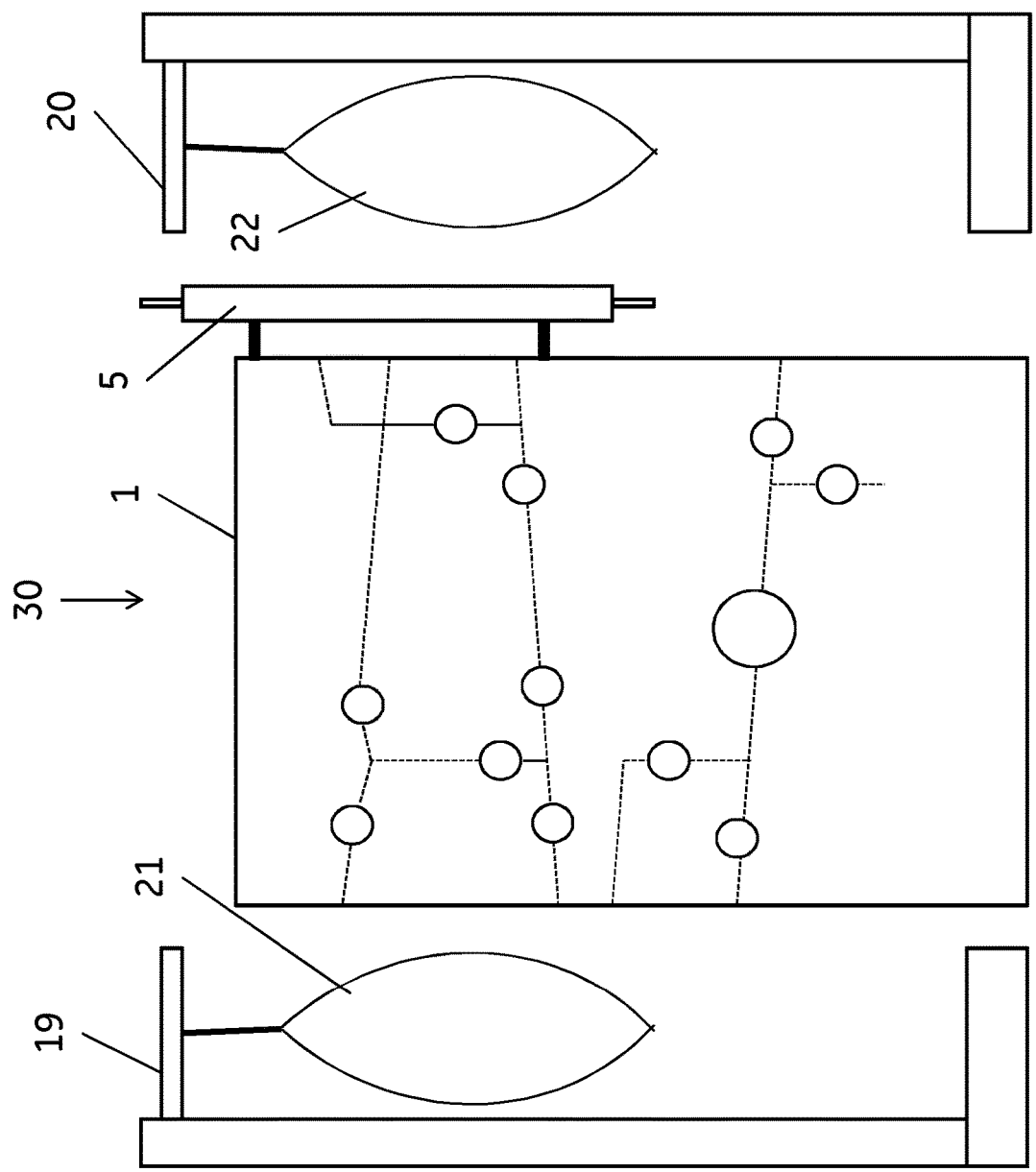
FIG. 4 shows an apparatus of the invention (front view).
Figure 5:
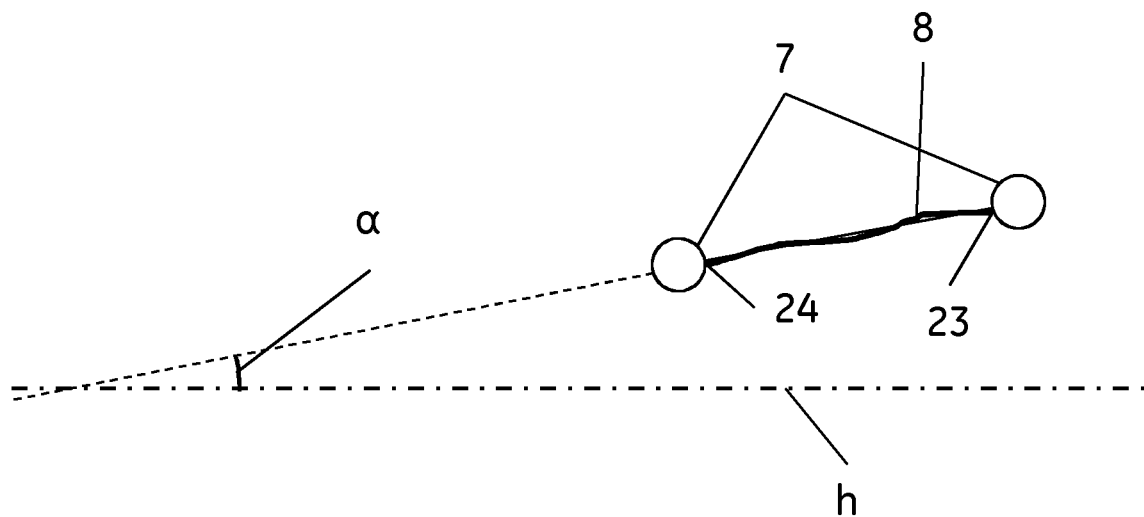
FIG. 5 shows a schematic picture of the slope calculation.
Figure 6:
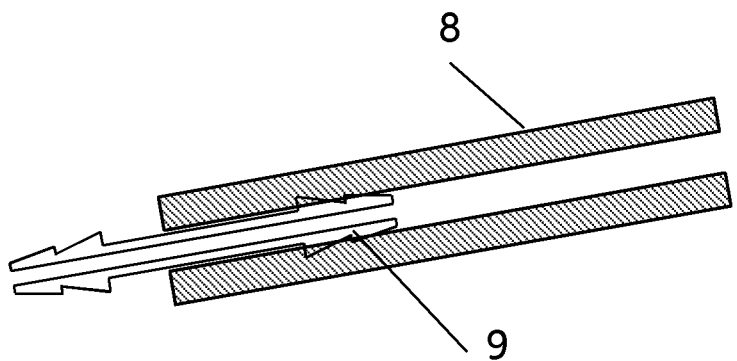
FIG. 6 shows part of a flow path leg with a hose barb connector.

In some embodiments, illustrated by FIG. 4, the first unit is adapted to be juxtaposed by the first lateral face against a second unit 19. The first unit can also be adapted to be juxtaposed by the second lateral face against a third unit 20. At least one of the second and third units may be adapted to receive a tank, such as a flexible bag 21,22, fluidically connected to the disposable flow path. One of the second and third units may e.g. be adapted to receive a feed/retentate tank or bag 21 and the other of the second and third units may e.g. be adapted to receive a permeate tank or bag 22. Alternatively, one of the second and third units may be adapted to receive both a feed/retentate tank or bag and a permeate tank or bag. The other of the second and third units may e.g. be adapted to receive a filtration element, e.g. a cassette holder for flat sheet filtration cassettes.

In a second aspect, illustrated by FIG. 4, the invention discloses an apparatus 30 for treatment of a bioprocess liquid. The apparatus can typically be a filtration apparatus, such as a tangential flow filtration apparatus, but it can also be e.g. a chromatography apparatus. This apparatus comprises the first unit 1 as discussed above and at least one of a second 19 and a third 20 unit juxtaposed by the first and/or second lateral faces. The apparatus may further comprise one or more of a filtration element 5, a feed/retentate tank or bag 21 and a permeate tank or bag 22, all of which may be fluidically connected by the disposable flow path 6 described above. The disposable flow path may comprise a retentate loop received by a retentate pump and fluidically connected with a retentate inlet and a retentate outlet on the filter element. The retentate loop can also suitably be fluidically connected with a feed/retentate tank or bag, such as with a feed/retentate tank or bag outlet and a feed/retentate tank or bag inlet. Further, the disposable flow path may comprise a permeate line or permeate loop fluidically connected to at least a permeate outlet on the filter element. The permeate line/loop may be received by a permeate pump and fluidically connected to a permeate tank or bag.

In a third aspect, the invention discloses a method of installing a disposable flow path on the first unit as discussed above, comprising receiving the disposable flow path in the valves and optional pumps and sensors, wherein one or more, such as all, legs of said disposable flow path have a slope of at least 3.0, such as at least 4.0, degrees from the horizontal plane. Suitably, one or more legs have a slope of 3.0-10.0, 3.0-8.0 or 4.0-6.0 degrees from the horizontal plane. The disposable flow path can be supplied presterilized, e.g. sterilized by gamma irradiation. It can be equipped with sanitary connectors for aseptic connection to a filtration element, a feed/retentate tank or bag and a permeate tank or bag. Alternatively, it can comprise lengths of tubing for sterile welding to tubing extending from the filtration element, feed/retentate tank/bag and or permeate tank/bag.

In a fourth aspect, the invention discloses a method of tangential flow filtration of a bioprocess liquid, comprising the steps of:
a) providing the apparatus as discussed above;
b) circulating the liquid from the feed/retentate tank or bag through a retentate loop of the disposable flow path and the filtration element and back to the feed/retentate tank or bag;
c) conveying a permeate from the filtration element through a permeate line or permeate loop of the disposable flow path either to the permeate tank or bag or to a drain.

The method can also comprise, before or during step b), a step a') of letting out any residual air through an air outlet leg of the disposable flow path. The air outlet leg may be a branch of the flow path located in a high position and may comprise a sterilization grade filter to prevent contamination of the flow path.

In some embodiments, the method comprises, after step c), a step d) of draining the disposable flow path. The draining can e.g. be performed via a draining leg of the disposable flow path. This leg can e.g. be a branch of the flow path located in a low position and it may be connected to a drain vessel. After the draining step d), the method may further comprise a step e) of discarding the disposable flow path. This can e.g. be done by incineration.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if they were individually incorporated.

The invention claimed is:

1. A first unit for treatment of a bioprocess liquid comprising a first lateral face, a second lateral face and a front face which meets the two said lateral faces; said front face comprising: a plurality of valves adapted to receive and act upon one or more legs of a disposable flow path; wherein said plurality of valves receiving legs of the disposable flow path connected by hose barb couplings are vertically offset from each other in a plane along the front face to give all legs of the disposable flow path connected by hose barb couplings received by said valves a slope of at least 4.0 degrees from a horizontal plane.

2. The first unit of claim 1, wherein said valves are arranged to give all legs of said disposable flow path a slope of up to 10 degrees from the horizontal plane.

3. The first unit of claim 1, further comprising pumps and sensors.

4. The first unit of claim 1, further adapted to receive a filter element fluidically connected to said disposable flow path.

5. The first unit of claim 1, wherein said plurality of valves comprises one or more pinch valves.

6. The first unit of claim 3, wherein the pumps comprise peristaltic pumps.

7. The first unit of claim 1, further comprising guides on said front face between said valves for installation of said disposable flow path, wherein said guides are essentially linear with slopes of at least 4 degrees from the horizontal plane.

8. The first unit of claim 7, wherein said guides comprise visually and/or tactilely distinguishable lines.

9. The first unit of claim 7, wherein said guides comprise pegs, ledges and/or recesses adapted to receive said disposable flow path.

10. The first unit of claim 1, further comprising a processor with an optical display, wherein a graphical user interface on said optical display shows an outline of said front face with valves and the flow path.

11. The first unit of claim 1, which is a tangential flow filtration unit.

12. The first unit of claim 1, which is a chromatography unit.

13. The first unit of claim 1, which is a bioreactor.

14. The first unit of claim 1, adapted to be juxtaposed by the first lateral face against a second unit.

15. The first unit of claim 14, adapted to be juxtaposed by the second lateral face against a third unit.

16. The first unit of claim 15, wherein at least one of said second and third units is adapted to receive a tank fluidically connected to said disposable flow path.

17. The first unit of claim 1, further comprising a disposable flow path received by said plurality of valves.

18. The first unit of claim 17, wherein the legs of said flow path are aligned with guides.

19. The first unit of claim 17, wherein said disposable flow path comprises at least one air outlet leg and/or at least one draining leg.

20. An apparatus for treatment of a bioprocess liquid, comprising the first unit of claim 1 and at least one of a second and a third unit juxtaposed by the first and/or second lateral faces.

21. The apparatus of claim 20, further comprising one or more of a filtration element, a feed/retentate tank or bag and a permeate tank or bag.

22. The apparatus of claim 20, further comprising the disposable flow path.

23. The apparatus of claim 22, wherein said disposable flow path provides fluidical connection between a filtration element and at least one of a feed/retentate tank or bag and a permeate tank or bag.

24. A method of installing a disposable flow path on the first unit of claim 1, comprising receiving said disposable flow path in said valves, wherein all legs of said disposable flow path have a slope of at least 4 degrees from the horizontal plane.

25. The method of claim 24, wherein said disposable flow path comprises at least one air outlet leg and/or at least one draining leg.

26. The method of claim 24, wherein the legs of said flow path are aligned with guides.

27. The method of claim 24, wherein said disposable flow path is presterilized.

28. A method of tangential flow filtration of a bioprocess liquid comprising the steps of:
a) providing the apparatus of claim 23;
b) circulating said liquid from said feed/retentate tank or bag through a retentate loop of said disposable flow path and said filtration element and back to said feed/retentate tank or bag;

c) conveying a permeate from said filtration element through a permeate line or permeate loop of said disposable flow path either to said permeate tank or bag or to a drain.

29. The method of claim 28, comprising, before or during step b), a step a') of letting out residual air through an air outlet leg of said disposable flow path.

30. The method of claim 28, comprising, after step c), a step d) of draining said disposable flow path.

31. The method of claim 30, comprising, after step d), a step e) of discarding said disposable flow path.

32. The first unit of claim 1, further comprising one or more sensors adapted to receive and to measure one or more parameters in one or more legs of said disposable flow path, wherein said plurality of valves and one or more sensors receiving the legs of the disposable flow path are vertically offset from each other in the plane along the front face to give all legs of the disposable flow path connected by hose barb couplings received by said valves and sensors the slope of at least 4.0 degrees from the horizontal plane.

33. The first unit of claim 1, further comprising one or more pumps adapted to receive and act upon one or more legs of said disposable flow path, wherein said plurality of valves and one or more pumps receiving the legs of the disposable flow path are vertically offset from each other in the plane along the front face to give all legs of the disposable flow path connected by hose barb couplings received by said valves and pumps the slope of at least 4.0 degrees from the horizontal plane.

* * * * *